(12) United States Patent
Kvist

(10) Patent No.: US 12,161,144 B2
(45) Date of Patent: Dec. 10, 2024

(54) PROCESS FOR PREPARATION OF CEREAL FRACTIONS

(71) Applicant: CREAL FOOD AB, Viken (SE)

(72) Inventor: Sten Kvist, Ödåkra (SE)

(73) Assignee: CREAL FOOD AB, Viken (SE)

( * ) Notice: Subject to any disclaimer, the term of this patent is extended or adjusted under 35 U.S.C. 154(b) by 655 days.

(21) Appl. No.: 17/297,512

(22) PCT Filed: Nov. 29, 2019

(86) PCT No.: PCT/EP2019/083068
§ 371 (c)(1),
(2) Date: May 27, 2021

(87) PCT Pub. No.: WO2020/109541
PCT Pub. Date: Jun. 4, 2020

(65) Prior Publication Data
US 2022/0007693 A1    Jan. 13, 2022

(30) Foreign Application Priority Data
Nov. 29, 2018    (SE) ..................... 1851490-1

(51) Int. Cl.
*A23L 7/104* (2016.01)
*A23L 2/52* (2006.01)
(Continued)

(52) U.S. Cl.
CPC .................. *A23L 7/107* (2016.08); *A23L 2/52* (2013.01); *A23L 5/15* (2016.08); *A23L 7/115* (2016.08); *A23L 23/00* (2016.08)

(58) Field of Classification Search
CPC . A23L 33/21; A23L 7/115; A23L 2/52; A23L 7/107; A23L 23/00; A23L 29/35; A23L 5/15; C08B 30/18; C08B 37/0003; C08B 30/042; C08B 37/0024; A23J 3/227; A23J 1/125; C08H 8/00; C08L 5/00;
(Continued)

(56) References Cited

U.S. PATENT DOCUMENTS 4,428,967 A    1/1984    Goering et al.
4,996,063 A    2/1991    Inglett
(Continued)

FOREIGN PATENT DOCUMENTS

EP    2108267 A1    10/2009
EP    1133551 B1    5/2010
(Continued)

OTHER PUBLICATIONS

Bell, Stacey et al., "Effect of Beta-Glucan from Oats and Yeast on Serum Lipids", Critical Reviews in Food Science and Nutrition, vol. 39, 2.
(Continued)

*Primary Examiner* — Subbalakshmi Prakash
(74) *Attorney, Agent, or Firm* — Renner, Otto, Boisselle & Sklar, LLP

(57) ABSTRACT

A process for preparation of cereal fractions. The process comprises wet milling of oat grains or barley grains in the presence of an enzyme composition derived from malt; and when oat grains or barley grains are wet milled, optionally isolating, from the wet milled grains, a beta-glucan enriched fraction. Liquid and solid food products obtainable by the process.

16 Claims, 3 Drawing Sheets

(51) Int. Cl.
*A23L 5/10* (2016.01)
*A23L 7/10* (2016.01)
*A23L 23/00* (2016.01)

(58) Field of Classification Search
CPC . C08L 89/00; C08L 3/02; C08L 91/00; C12N 9/2414; C12Y 302/01001
USPC ............................................................. 426/29
See application file for complete search history.

(56) References Cited

U.S. PATENT DOCUMENTS

| | | | |
|---|---|---|---|
| 5,458,893 | A | 10/1995 | Smith |
| 5,686,123 | A | 11/1997 | Lindahl et al. |
| 6,168,821 | B1 | 2/2001 | Castleberry |
| 6,323,338 | B1 | 11/2001 | Fisher et al. |
| 2005/0089602 | A1 | 4/2005 | Kvist et al. |
| 2010/0112127 | A1 | 5/2010 | Chatel et al. |

FOREIGN PATENT DOCUMENTS

| | | |
|---|---|---|
| EP | 1706001 A1 | 6/2011 |
| JP | 2009207359 A | 9/2012 |
| WO | 92/10106 A1 | 6/1992 |
| WO | 00/24270 A1 | 5/2000 |
| WO | 00/24864 A1 | 5/2000 |
| WO | 0154519 A1 | 8/2001 |
| WO | 02/02645 A1 | 1/2002 |
| WO | 2005/048735 A1 | 2/2005 |
| WO | 2014/123466 A1 | 8/2014 |
| WO | 2016/124626 A1 | 8/2016 |
| WO | 2016/124608 A1 | 11/2016 |
| WO | 2018/219869 A1 | 6/2018 |
| WO | 2018/219866 A1 | 12/2018 |

OTHER PUBLICATIONS

Keying Q et al: "An investigation on pretreatments for inactivation of lipase in naked oat kernels using microwave heating", Journal of Food Engineering, Barking, Essex, GB, vol. 95, No. 2, Nov. 1, 2009 {Nov. 1, 2009), pp. 280-284, XP026419541, ISSN : 0260.
Foster-Powell and Brand Miller, "International tables of glycemic index", Am J. Clin. Nutr., 62, 871S-893S, 1995.
International Search Report and Written Opinion mailed Mar. 3, 2020 for corresponding International Application No. PCT/EP2019/083068.
Communication pursuant to Article 94(3) EPC dated Oct. 12, 2023, for European Patent Application No. 19813476.9.

PROCESS FOR PREPARATION OF CEREAL FRACTIONS

This application is a national phase of International Application No. PCT/EP2019/083068 filed Nov. 29, 2019, which claims priority to Swedish Application No. 1851490-1 filed Nov. 29, 2018, both of which are hereby incorporated herein by reference in their entireties.

TECHNICAL FIELD

The present invention relates to a process for preparation of cereal fractions, the process comprising wet milling. The present invention also relates to liquid and solid food products.

BACKGROUND ART

There are acknowledged health and nutritional benefits for humans in increasing the daily intake of soluble dietary fibres from oat and barley grains. In particular, the beta-glucan component of these cereals has been related and directly linked to a number of beneficial effects, for example a demonstrated reduction of serum cholesterol levels, alongside improvements in HDL/LDL ratios in the blood, an effect strongly correlated with improved cardiovascular health in humans (Bell et al, Critical Reviews in Food Science and Nutrition, Vol 39, 2, 1999). Additionally, highly viscous (and usually high molecular weight) non-starch polysaccharides present in whole cereal grains may be implicated in mechanisms regulating blood glucose, with an implied beneficial effect in long term prevention of type 2 diabetes (Foster-Powell and Brand Miller, Am J. Clin. Nutr., 62, 871S-893S, 1995).

Of further significance, the soluble dietary fibres present in oat and barley are not digested in the human intestine and therefore pass through to the colon where they are available for microbial fermentation and as such are effective prebiotic materials. Additionally, barley and oats comprise several other nutritional components of great value. Thus, native proteins, non-gelatinized starch and fat are important components.

Furthermore, the soluble beta-glucans from oats and barley are very interesting as functional ingredients in foods as they exhibit gelling behaviour, stabilizing properties, water binding and impart good mouth feel to products. High molecular weight beta-glucans have potential as viscosity modifiers, colloidal stabilizers, texturizers etc. in foodstuffs.

Most processes claiming to produce compositions containing high concentrations of soluble dietary fibers from oat and barley grain are based on alkaline extraction either from milled whole grain or a sieved fraction (Fisher et al, U.S. Pat. No. 6,323,338) or even on hot water extraction, which yields lower molecular weight soluble beta-glucans (Morgan, WO 02/02645).

Inglett (U.S. Pat. No. 4,996,063 and WO 92/10106) describes methods to produce water-soluble dietary fibre compositions from milled, heat treated oat flours and milled barley flours, via treatment with alpha-amylase enzymes to degrade starch components and subsequent centrifugation to remove insoluble materials from the hydrolysate mixture.

Lindahl et al (U.S. Pat. No. 5,686,123) inform on methods to produce soluble cereal suspensions from oat. The basis of the invention is treatment of previously heat-treated ground oat, with alpha-amylase class of enzyme, whilst slurred in water.

Triantafyllou (WO 00/24270) describes a method to produce beta-glucan soluble dietary fibre from heat-treated oat flour, using alpha-amylase enzyme to hydrolyze starch to lower molecular weight fragments.

EP 1 706 001 discloses a method for preparing beta-glucans from oat where non-heated oat grains were dry milled and 50% by weight of the grain was retained as a coarser fraction. This coarser material was suspended in water at a temperature of 95° C. and alpha-amylase enzyme was added to the suspension.

For many of the nutraceutical and functional applications, it is crucial to maintain high molecular weights in the beta-glucan component of the soluble fibre and to isolate the soluble dietary fibre cost-effectively with a reasonably high concentration of beta-glucan in the isolate. This "double challenge" is addressed in the present invention.

SUMMARY OF THE INVENTION

It is an object of the present invention to provide cereal fractions of high nutritional value. It is another object of the present invention to provide cereal fractions of high health value. It is an additional object of the present invention to provide cereal fractions of high technological value. It is thus an object of the invention to provide cereal fractions that are suitable for further processing and/or that may be used for modifying the rheological properties of products such as food or cosmetics. It is a further object of the present invention to provide cereal fractions of high sensorical quality. It is thus an object of the invention to provide cereal fractions having a good taste and mouth-feel.

A particular object also accomplished by the invention is to facilitate wet milling of oat grains or barley grains. In this context, grains are to be understood as whole grains or as cut grains. The outer layer of a grain is known as bran and is rich in dietary fiber and essential fatty acids. The bran encloses the endosperm, which contains starch (in the form of starch granules), fatty acids and protein.

These objects as well as other objects of the invention, which should become apparent to a person skilled in the art after having studied the description below, are accomplished by a process for preparation of cereal fractions, comprising the following step:

b) wet milling of oat grains or barley grains, in the presence of an enzyme composition derived from malt; and optionally, isolating, from the wet milled grains, a beta-glucan enriched fraction.

The wet milling of the grains is performed in the presence of an enzyme composition derived from malt. The term "enzyme composition derived from malt" designates herein a combination of enzymes derived from malt, wherein the enzymes may be isolated from malted grain or may be present in or together with malted grain. Enzymes present in malt are several. Starch degrading enzymes are alpha-amylase, beta-amylase, limit dextrinase, and alpha-glucosidase. Beta-glucan degrading enzymes are endo-1,4-glucanase and endo-1,3-glucanase. A protein degrading enzyme is exopeptidase. Presence of the enzyme composition derived from malt facilitates the wet milling, in particular the separation of bran components from each other, by lowering the viscosity of the slurry being wet milled and by shortening the process time necessary for the separation.

The wet milling may be performed for 5-30 minutes, 5-20 minutes, such as 5-15 minutes, such as 5-10 minutes.

The wet milling, in presence of the enzyme composition derived from malt, may occur, continuously or intermittently, for 30 minutes or less, preferably 20 minutes or less, such as 15 minutes or less.

The wet milling increases the surface of the grains and thereby the amount of substrate available to the enzyme composition.

The limited time, 5-30 minutes as described above, of wet milling contributes to ensure that the beta-glucans maintain their high molecular weight, at about 3 000 000 Da.

Presence of the enzyme composition derived from malt may not substantially affect the molecular weight of the beta-glucans. The present invention may thus provide a soluble fibre rich fraction wherein the native molecular weight of the separated beta-glucans is substantially maintained or wherein more than 50%, preferably more than 75%, of the weight average molecular weight is maintained. The molecular weight of beta-glucans separated from other bran components may, for different enzyme sources and as a function of process time, be studied by HPLC (high pressure liquid chromatography).

The temperature of the wet milling step may be 68 to 78° C., such as 72 to 76° C., such as 75° C.

The wet milling in presence of the enzyme composition derived from malt may be followed, typically before isolation of sub fraction(s) from the wet-milled grains, by inactivation of said enzyme composition, such as by heat treatment of the wet-milled grains, preferably at 100° C. or above.

By the wet milling of step b) a mechanical processing of the slurry is obtained, wherein the grains, i.e. the bran tissue, the endosperm tissue and the starch granules, are torn apart and large surfaces are created that allow for the different molecules in the system to find each other. The wet milling may be performed by a toothed colloid mill (available, e.g., from Fryma).

The wet milling of step b) may be performed at a ratio of grain to water in the range of 1:1 to 1:12, preferably below 1:10, below 1:8, below 1:7, below 1:6, below 1:5 or below 1:4 (weight:weight). The viscosity or the consistency of a resulting product may thus be adjusted already during step b). Alternatively, drying of a resulting product may be facilitated by a low water content during step b).

The product of subjecting grains to the wet milling of step b) may be separated into different fractions and used e.g. as or for a fibre rich and beta-glucan rich liquid food product (originating from the bran of the grains), typically of high consistency; as or for a dextrin rich and protein rich liquid food product (originating from the endosperms of the grains), typically of low consistency; and as or for a dextrin rich liquid food product (originating from the starch granules), typically of low consistency. Each of these liquid food products may be a drink or a soup. Each of these liquid food products can easily be modified by adding taste enhancers or by adding probiotics.

In step b) the malt may be selected from the group consisting of oat malt, barley malt or a combination thereof. It is preferred that oat malt is used for the wet milling of oat grains. It is preferred that barley malt is used for the wet milling of barley grains. By such preferred uses contamination of an oat based or barley based product, respectively, with another cereal is avoided.

The activity of one or more of beta-glucanase, beta-amylase, limit dextrinase and alpha-glucosidase present in said enzyme composition derived from malt may be reduced or eliminated, preferably while essentially maintaining the activity of alpha-amylases present in said enzyme composition derived from malt, before the enzyme composition is provided to the wet milling of step b). The viscosity of the slurry being wet milled is lowered under influence of alpha-amylase.

The enzyme composition may be heat treated, preferably at a temperature in the range of 75 to 80° C., before being provided to the wet milling of step b). Such heat treatment activates the alpha-amylase enzymes of the malt and reduces the activity of other malt enzymes present. The enzyme composition may be heat treated for 1 to 15 minutes, preferably for 3 to 12 minutes.

The enzyme composition may be a malt extract or comminute malt grains, preferably a malt extract. The malt extract can be used in an amount of 2 to 5 wt % of the weight of the grains. The malt extract may be obtained by crushing malt grains and extracting enzymes into a water phase. Malt grains need not be removed from the enzyme composition if it will be satisfactorily milled in the wet milling of step b).

Step b) of wet milling may be performed more than once. Preferably, a new amount of enzyme composition is added before, at the start of or during the wet milling.

Each step b) of wet milling may be performed for 5-30 minutes, 5-20 minutes, such as 5-15 minutes, such as 5-10 minutes. Thus, the oat grains or barley grains are wet milled for totally 15-90 minutes, 15-60 minutes, 15-45 minutes.

An advantage of performing step b more than once is that a better effect is achieved than if the wet milling were to be performed in one longer continuous step. Furthermore, when a new amount of the enzyme composition is added for each consecutive step of wet milling, the presence of active enzymes is ensured.

Thus, the time period for each step of wet milling can be relatively short, giving a shorter total milling time than if only one longer step of wet willing were to be performed.

Step b) of wet milling may be performed more than once, such as two, three, four, five or six times.

Thus, in one embodiment, step b) is performed more than one time.

Thus, in one embodiment, step b) is performed more than two times.

Thus, in one embodiment, step b) is performed more than three times.

Thus, in one embodiment, step b) is performed more than four times.

Thus, in one embodiment, step b) is performed more than five times.

Thus, in one embodiment, step b) is performed more than six times.

Step b) of wet milling may be performed two times.
Step b) of wet milling may be performed three times.
Step b) of wet milling may be performed four times.
Step b) of wet milling may be performed five times.
Step b) of wet milling may be performed six times.

In one preferred embodiment, step b) is performed three times.

In another preferred embodiment, step b) is performed four times.

The temperature of the wet milling steps may be between 68 to 78° C., such as 72 to 76° C., such as 75° C.

The temperature of the wet milling steps may be performed at the same temperature.

The temperature of the wet milling steps may be performed at different temperatures.

The temperature may be lowered between each step of wet milling. Preferably, the temperature is lowered 3-5° C., such as 4° C., between each step of wet milling. Different enzymes have different temperature ranges where they have their activity optimum. Thus, by lowering the temperature in each step of wet milling, different enzymes are allowed to break down substances in the grains. Thus, higher yield of the beta-enriched fraction is achieved. In addition a better taste of the final product is achieved.

Thus, in one embodiment, the first step of wet milling is performed at 78° C., the second step of wet milling is performed at 73° C. and the third step of wet milling is performed at 69° C. The beta-glucan enriched fraction may be isolated by removing, from the wet milled grains, a fibre enriched fraction. The fibre enriched fraction may optionally dried.

Thus, step b) may further comprise isolating, from the wet milled grains, a beta-glucan enriched sub fraction. The beta-glucan enriched sub fraction may be isolated by removing, from the wet milled grains, a fibre enriched sub fraction. The isolation of the beta-glucan enriched sub fraction is typically performed by decanting. The viscosity of the beta-glucan enriched sub fraction can be modified by changing the proportions of water and grains before the grains are wet milled or in the wet milled grain fraction. The beta-glucan enriched sub fraction can be used as or for a liquid food product, such as a drink or soup. The liquid food product can easily be modified by adding taste enhancers or by adding probiotics. The viscosity of the liquid food product can be increased by adding a more concentrated beta-glucan product, wet or dry. The fibre enriched sub fraction may optionally be dried, typically in a ring dryer. The fibre enriched sub fraction can be used for production of an extruded food product, such as a meat substitute.

The process may further comprise isolating, from the fibre enriched sub fraction, a component enriched in protein and fat. It is preferred to dry the fibre enriched sub fraction before isolating the component enriched in protein and fat. The isolation may typically be performed by sieving. Thus, protein and fat can be collected as one fraction.

The process may further comprise isolating, from the beta-glucan enriched sub fraction, a component further enriched in beta-glucan and a component enriched in dextrins, and optionally drying the component further enriched in beta-glucan and/or the component enriched in dextrins. Such isolation is typically performed in a centrifugal separator. The component further enriched in dextrins is typically dried in a spray drier, preferably after evaporation. The component further enriched in beta-glucan is typically dried in a drum drier. The component further enriched in beta-glucan may be added to the beta-glucan enriched sub fraction in order to raise its viscosity.

It is possible to perform the isolation of step b) by use of a three-phase decanter. One obtains three phases, a solid phase comprising fibre, protein and fat, and two individual liquid phases comprising dextrins and beta-glucans, respectively. Isolation is thus performed in one step, which means that the process is shortened and that beta-glucans come out of the process faster and can be pumped to the dryer. One thus obtains a high molecular weight of the beta-glucans due to the short processing time.

An alternative to the use of the three-phase decanter is the use of a two-phase decanter and a centrifugal separator. One obtains from the two-phase decanter a solid phase comprising fibre, protein and fat and a liquid phase comprising dextrines and beta-glucans. The liquid phase may be passed through a centrifugal separator. One obtains from the separator a phase comprising dextrins and one phase comprising beta-glucans.

The wet milled grains may alternatively be decanted to form a sub fraction enriched in beta-glucan and dextrin, a sub fraction enriched in protein and fat and a sub fraction enriched in fibre.

The process may further comprise a step a) of providing oat grains or barley grains for use in step b) by subjecting oat grains or barley grains to a dry heat treatment reducing lipase activity.

The oat grains or barley grains are preferably of a variety with high content of beta-glucans. The oat grains or barley grains may be traditional or organic. The reception of grains is preferably of high quality, good hygienic condition and/or substantially dust-free. The grains may be stored in silos. Before entering step a), the oat grains or barley grains are preferably cleansed. Cleansing may comprise removal of stones and dirt and/or sorting out seeds of another species, such as non-oat grains and/or non-barley grains. Before entering step a), the oat grains are preferably dehulled and separated from the hulls.

Grains may contain a high content of fat. Oat grains may contain >5% fat. The dry heat treatment of step a) may reduce enzyme activity, in particular it reduces lipase activity, in the oat grains or barley grains. Due to the reduced enzyme activity, in particular the reduced lipase activity, the oat grains or barley grains, or any product or fraction derived thereof, become stable towards oxidation and development of rancidity. In the present process any dry heat treatment reducing lipase activity may be used. The term "dry" is used herein to designate a heat treatment wherein heat is transferred to the grains without contacting the grains with water or steam. A number of dry heat treatments suitable for grains are conceivable, such as heat treatments wherein heat is transferred to the grains by contacting the grains with hot air or by irradiation of a suitable wavelength. By applying a dry heat treatment there is no influence of water or steam on the starch content or the proteins, so the starch may remain substantially non-gelatinized and the proteins may remain partially or substantially non-denatured. The heat treatment of step a) may thus maintain starch in a substantially non-gelatinized condition and/or maintain proteins in a partially or substantially non-denatured condition.

In the dry heat treatment of step a) the core of the grains may be heated to a temperature of at least 60° C., preferably to a temperature in the range of 60 to 80° C. At this temperature range lipase activity will be reduced, while sensorical and functional properties of the grains are maintained.

The dry heat treatment of step a) may be performed by micro-wave technology or by the use of a heat exchanger, such as against hot air or against steam.

Heating of the grains by any one of the methods above, typically at their native water content, causes inactivation of the enzymes without gelatinization of the starch in the oat or barley kernel. The heat treatment of step a) may thus maintain starch in a substantially non-gelatinized condition and/or maintain proteins in a partially or substantially non-denatured condition.

According to one embodiment, oat grains and barley grains are wet milled together in step b).

According to a second aspect of the present invention, a liquid food product, such as a drink or soup obtainable by processing of oat or barley grains according to the process of the present invention is provided. The liquid food product comprises oat or barley fibre and oat or barley beta-glucan.

According to a third aspect of the present invention, a solid food product, such as a meat substitute obtainable by processing of oat or barley grains according to the process of the present invention is provided. The solid food product comprises oat or barley fibre.

The present description thus provides a novel method for the preparation of cereal grain fractions, such as producing a beta-glucan enriched fraction starting from a oat or barley grain, which is optionally dry heat treated, which is milled and the grains are made subject to malt, such as barley and/or oat malt in an aqueous phase. The optional step of dry heat treatment is carried out under non-aqueous conditions, thereby leaving a substantially non-gelatinized starch and a partially or substantially non-denaturated protein content. The milled oat or barley retained has a high quality and will not become rancid as the lipases of the grain have been inactivated by the heat treatment. The described process thus facilities the retaining of high-molecular beta-glucans, non-gelatinized starch, non-denaturated protein, fat and/or fibres in different fractions due to the requested final use of the different fractions. Isolation of a reasonably clean fraction of soluble dietary fibre containing high molecular weight beta-glucan at appreciable concentrations facilitates the cost-effective further processing of the material to yield preparations of very high beta-glucan concentrations at high molecular weight, and to adjust molecular weight of the materials in a controlled manner to "tailor" final product properties.

BRIEF DESCRIPTION OF THE DRAWINGS

The invention will be described in the following with reference to the appended drawings.

DETAILED DESCRIPTION

Figure 1:
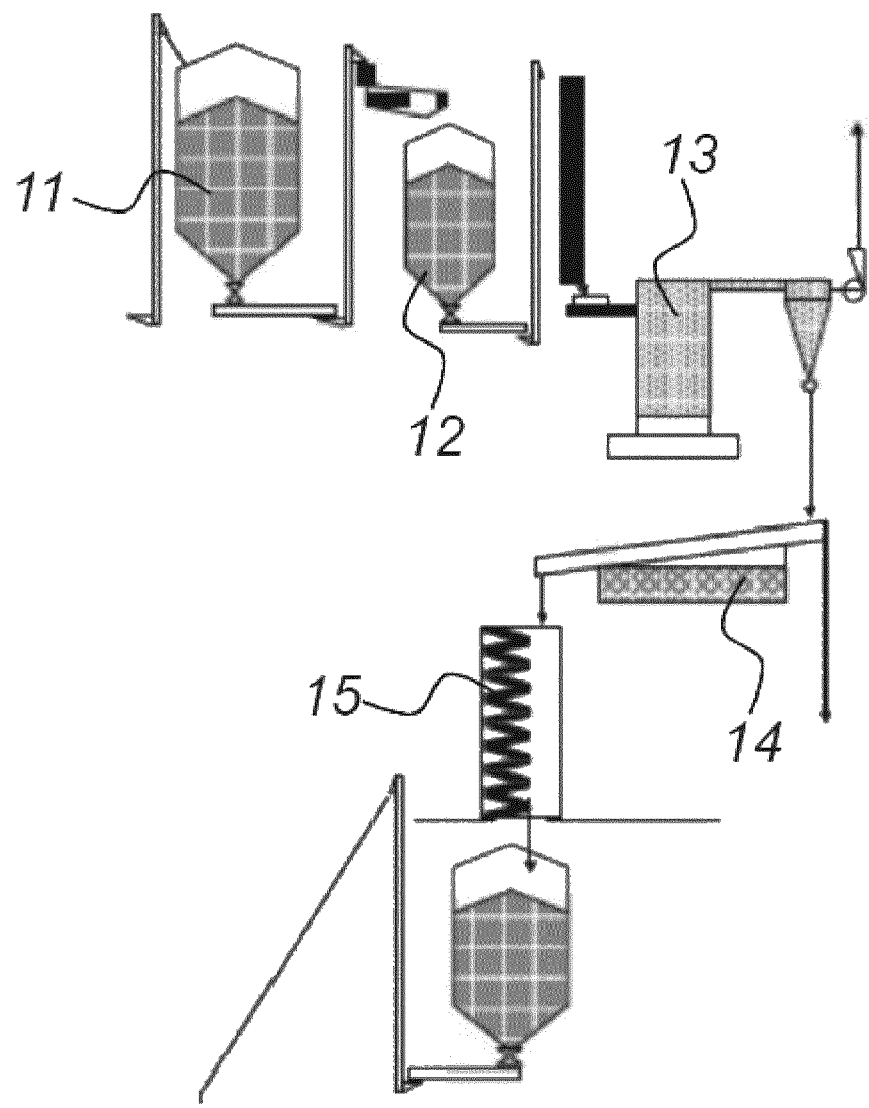
FIG. 1 shows schematically dry processing of grains.

FIG. 1 shows that oat grains or barley grains (hereinafter referred to as grains) are received into a silo 11 and are cleansed from dirt and gravel in a separator 12, whereupon the oat grains are transferred to a dehulling/dehusking apparatus 13. Dehulling/dehusking is only necessary for oats as being the only grain comprising a hull. The hull content is separated off on a shaking table 14, whereupon the grains are transferred to a heat treatment apparatus 15. The heat treatment apparatus 15 is, in this embodiment, a micro-wave apparatus tube, wherein the grains are made subject to a micro-wave heat treatment as described in WO 01/54519 A1. The dry heat treatment may alternatively be performed by the use of a heat exchanger, such as against hot air or against steam. The grains are heated to a temperature at which lipases present are deactivated, said temperature being about 60° C. in the centre or core of the grain, the grain core temperature, whereby an oat kernel is obtained that has a non-gelatinized starch content and may have a non-denaturated protein content.

Figure 2:
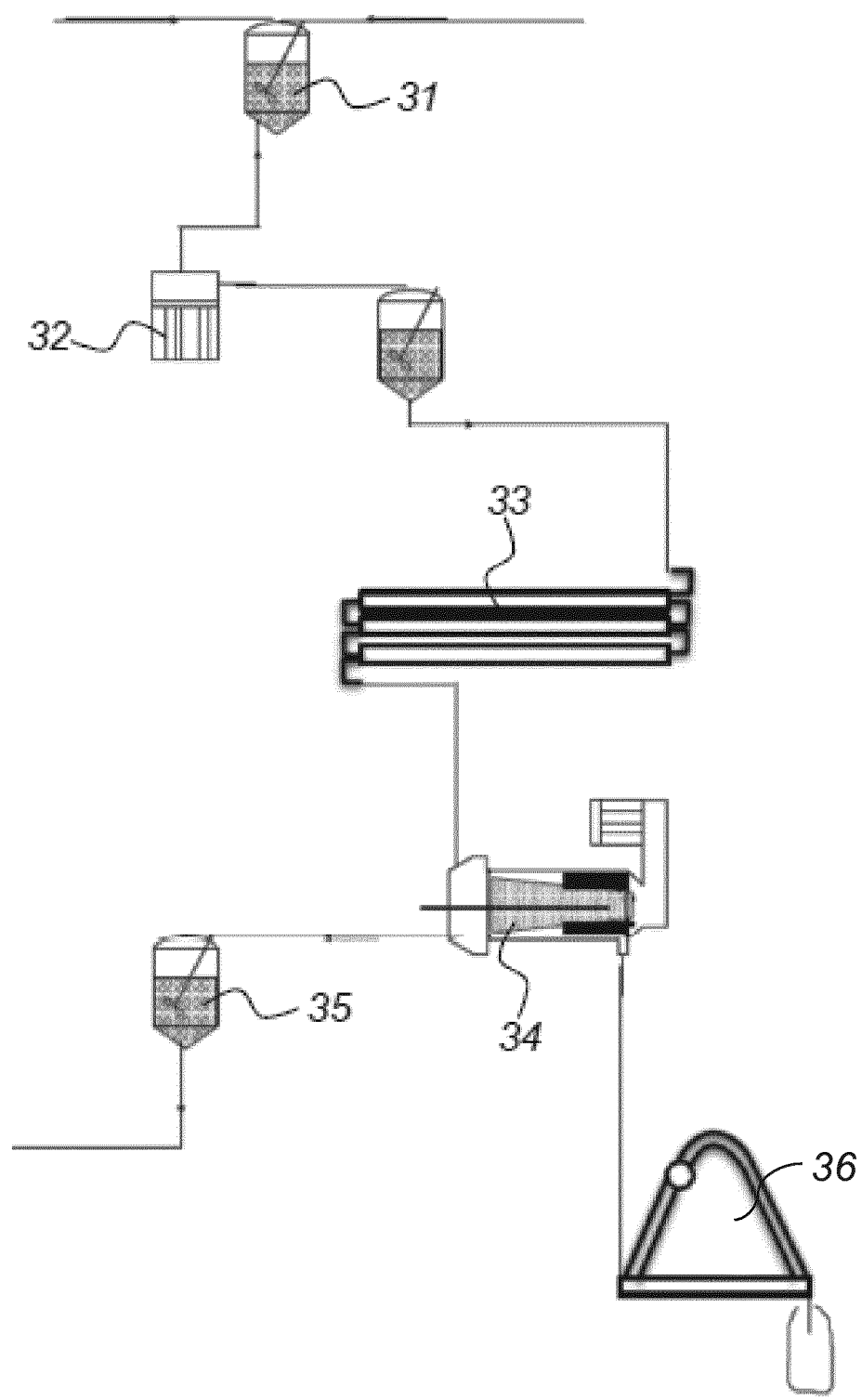
FIG. 2 shows schematically one embodiment of wet processing of oat grains or barley grains.

FIG. 2 shows a process, in which the grain fraction is mixed with water in a reaction vessel 31 together with malt or malt extract. After hydrolysis the slurry is made subject to a wet milling stage in a wet mill 32 and is further reacted with an additional amount of malt extract. Subsequently, the slurry is made subject to a heat treatment in a heat exchanger 33 at high temperature to deactivate any enzymes left. The slurry is then transferred to a decanter 34 to separate the fibres from an aqueous phase comprising carbohydrates, proteins, fat and beta-glucans. The fibres are transferred to a ring dryer 36 and dried. The aqueous phase is transferred to a tank 35 from which it can be transferred to a filling machine for filling of bottles or other packages for distribution to the market.

Figure 3:
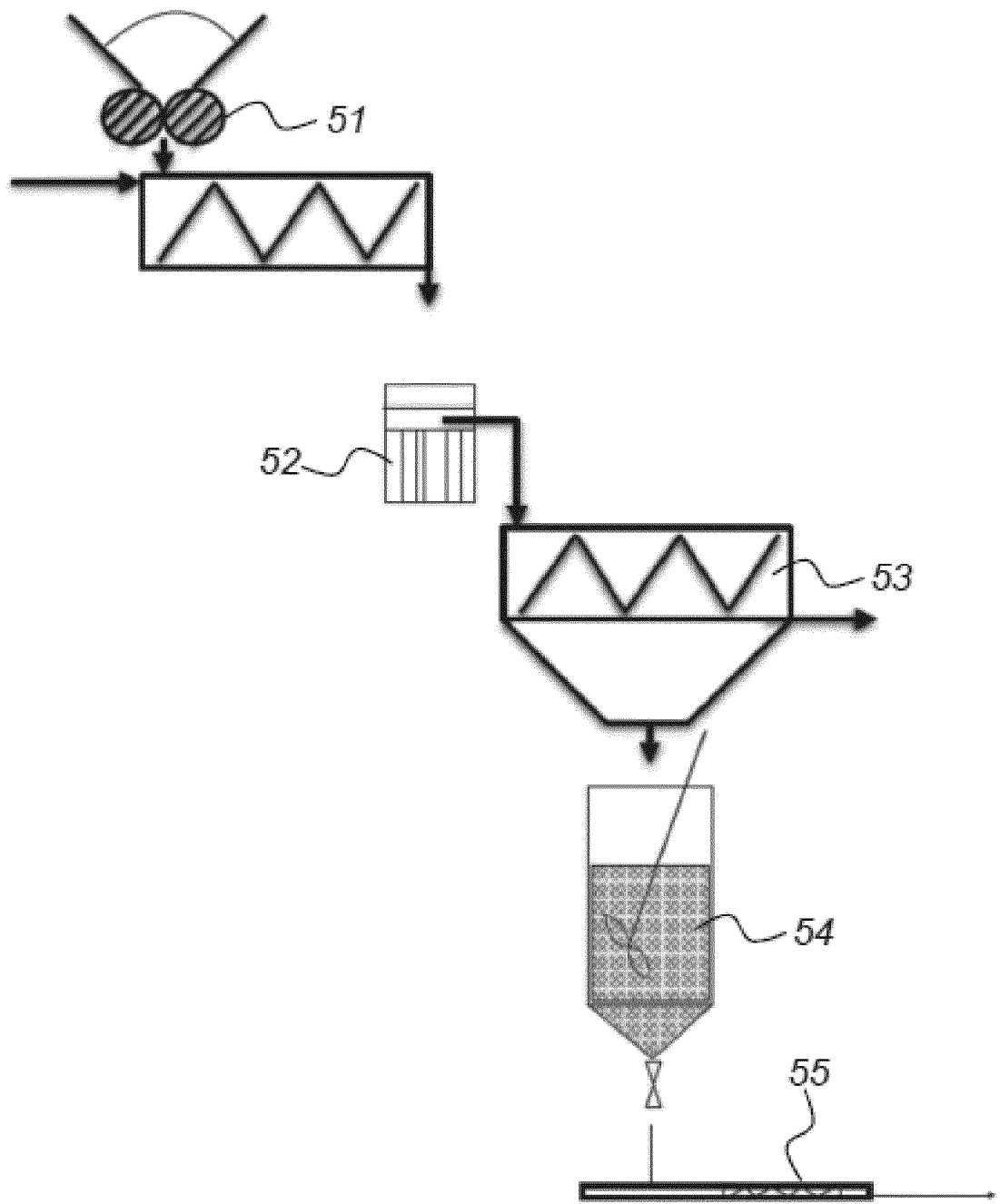
FIG. 3 shows schematically preparation of a malt extract.

FIG. 3 shows a process suitable to obtain a malt extract to be used in the wet processing described in connection with FIG. 2. Malt is milled in a mill 51 and then mixed in a mixer with water at an elevated temperature of 75° C. to 80° C. for 10 minutes. The malt is then homogenized in a wet mill 52, is sieved in a wet sieve 53, whereby a solid phase as well as an aqueous phase comprising enzymes are obtained. The aqueous phase, i.e. the malt extract, is transferred to a holding tank 54 held at 75 to 78° C. The malt extract is then added to the process, to vessel 21 or 31 of the wet processing of FIG. 2, respectively, via a malt pipe line 55 when needed.

EXAMPLE 1. WET PROCESSING OF GRAINS. FIBRE PRODUCT AND LIQUID OAT PRODUCT

A grain fraction, obtained by heat treatment of dehulled oat grains and subsequent cutting of the oat grains, was mixed with water in a ratio of about 1:5 by adding 3.6 kilograms of the grain fraction to 17 liters of water comprising oat malt in a boiling pan (a 100 liters Getinge cooking vessel) as follows.

The water was heated to 75° C., whereupon 1.7%, based on the weight of the grain fraction, of oat malt (60 grams) was added to the water in the boiling pan and the malt was mixed in the water. The cut grains (3.6 kg) were added under vigorous stirring to obtain an oat grain slurry, which was stirred vigorously for 5 minutes. The slurry was then wet-milled in a colloid mill (Fryma MZ) in a first step.

After the first wet milling step, the slurry was further stirred in the boiling pan for 5 minutes. An additional 1.7% of malt (60 grams) was added to the slurry. The slurry was stirred for 5 minutes at 75° C. The slurry was then made subject to a second wet-milling step in the colloid mill (Fryma MZ).

After the second wet milling step, the slurry was stirred in the boiling pan for another 5 minutes. An additional 1.7% of malt (60 grams) was added to the slurry. The slurry was then made subject to a third wet-milling step in the colloid mill (Fryma MZ).

After the third wet-milling step, the slurry was stirred for 10 minutes at 75° C. in the boiling pan, whereupon the slurry was heated to 100° C. with stirring. The slurry was then made subject to a fourth wet-milling step in the colloid mill (Fryma MZ).

The resulting oat slurry was decanted through a filter cloth (220 μm), whereby a solid fibre phase was removed. The solid fibre phase was subsequently dried in a drying cabinet at 105° C. for 8 hours and then milled into a powder.

The remaining liquid was a hydrolysed oat base having a pH of 6.3 and 13.8° Brix. About 15 kilograms of liquid oat product at a dry substance of about 13.8% was obtained. The liquid comprised carbohydrates, proteins, fat and beta-glucans and was a liquid drinkable oat product. The drinkable oat product was bottled in autoclaved bottles.

Itemized List of Embodiments

Item 1. A process for preparation of cereal fractions, comprising the following step:
b) wet milling of oat grains or barley grains in the presence of an enzyme composition derived from malt; and
isolating, from the wet milled grains, a beta-glucan enriched fraction.

Item 2. The process according to item 1, wherein in step b) the malt is selected from the group consisting of oat malt, barley malt or a combination thereof.

Item 3. The process according to item 1 or 2, wherein the activity of one or more of beta-glucanase, beta-amylase, limit dextrinase and alpha-glucosidase present in said enzyme composition derived from malt is reduced or eliminated, preferably while essentially maintaining the activity of alpha-amylases present in said enzyme composition derived from malt, before the enzyme composition is provided to the wet milling of step b).

Item 4. The process according to any one of the preceding items, wherein the enzyme composition is heat treated, preferably at a temperature in the range of 75 to 80° C., before being provided to the wet milling of step b).

Item 5. The process according to any one of the preceding items, wherein the enzyme composition is a malt extract or comminute malt grains, preferably a malt extract.

Item 6. The process according to any one of the preceding items, wherein the beta-glucan enriched fraction is isolated by removing, from the wet milled grains, a fibre enriched fraction, wherein the fibre enriched fraction is optionally dried.

Item 7. The process according to any one of the preceding items, further comprising isolating, from the beta-glucan enriched fraction, a component further enriched in beta-glucan and a component enriched in dextrins, and optionally drying the component further enriched in beta-glucan and/or the component enriched in dextrins.

Item 8. The process according to any one of items 6 to 7, further comprising isolating, from the fibre enriched fraction, a component enriched in protein and fat, and optionally drying the component enriched in protein and fat.

Item 9. The process according to any one of the preceding items, wherein the wet milled grains are decanted to form a fraction enriched in beta-glucan and dextrin, a fraction enriched in protein and fat and a fraction enriched in fibre.

Item 10. The process according to any one of items 1 to 9, further comprising the following step:
a) providing oat grains or barley grains for use in step b) by subjecting oat grains or barley grains to a dry heat treatment reducing lipase activity.

Item 11. The process according to item 10, wherein in the dry heat treatment of step a) the core of the grains is heated to a temperature of at least 60° C., preferably to a temperature in the range of 60 to 80° C.

Item 12. The process according to item 10 or 11, wherein the dry heat treatment of step a) is performed by micro-wave technology or by the use of a heat exchanger, such as against hot air or against steam.

Item 13. The process according to any one of item 10 to 12, wherein the dry heat treatment of step a) maintains starch in a substantially non-gelatinized condition and/or maintains proteins in a partially or substantially non-denatured condition.

Item 14. A liquid food product, such as a drink or soup, comprising oat or barley fibre and oat or barley beta-glucan, said food product being obtainable by processing of oat or barley grains according to the process of any of items 1 to 13.

Item 15. A solid food product, such as a meat substitute, comprising oat or barley fibre, said food product being obtainable by processing of oat or barley grains according to the process of any of items 1 to 13.

The invention claimed is:

1. A process for preparation of cereal fractions, comprising the following steps:

a) subjecting oat grains or barley grains to a dry heat treatment, wherein in the dry heat treatment the core of the grains is heated to a temperature of at least 60° C.;

b) wet milling of the oat grains or the barley grains resulting from step a) in the presence of an enzyme composition derived from malt, wherein the enzyme composition is heat treated at a temperature in the range of 75 to 80° C. before being provided to the wet milling of step b); and isolating, from the wet milled grains, a beta-glucan enriched fraction by removing, from the wet milled grains, an insoluble fibre enriched fraction.

2. The process according to claim 1, wherein in step b) the malt is selected from the group consisting of oat malt, barley malt or a combination thereof.

3. The process according to claim 1, wherein an activity of one or more of beta-glucanase, beta-amylase, limit dextrinase and alpha-glucosidase present in said enzyme composition derived from malt is reduced or eliminated, while essentially maintaining the activity of alpha-amylases present in said enzyme composition derived from malt, before the enzyme composition is provided to the wet milling of step b).

4. The process according to claim 1, wherein the enzyme composition is a malt extract or comminute malt grains.

5. The process according to claim 1, wherein step b) of wet milling is performed more than once.

6. The process according to claim 1, wherein step b) of wet milling is performed three times.

7. The process according to claim 1, wherein the insoluble fibre enriched fraction is dried.

8. The process according to claim 1, further comprising isolating, from the insoluble fibre enriched fraction, a component enriched in protein and fat, and optionally drying the component enriched in protein and fat.

9. The process according to claim 1, further comprising isolating, from the beta-glucan enriched fraction, a component further enriched in beta-glucan and a component enriched in dextrins, and optionally drying the component further enriched in beta-glucan and/or the component enriched in dextrins.

10. The process according to claim 1, wherein the wet milled grains are decanted to form a fraction enriched in beta-glucan and dextrin, a fraction enriched in protein and fat, and a fraction enriched in insoluble fibre.

11. The process according to claim 1, wherein in the dry heat treatment of step a) the core of the grains is heated to a temperature in the range of 60 to 80° C.

12. The process according to claim 1, wherein the dry heat treatment of step a) is performed by micro-wave technology or by the use of a heat exchanger.

13. The process according to claim 1, wherein the dry heat treatment of step a) maintains starch in a substantially non-gelatinized condition and/or maintains proteins in a partially or substantially non-denatured condition.

14. A process for preparation of cereal fractions, comprising the following steps:

a) subjecting oat grains and barley grains to a dry heat treatment, wherein in the dry heat treatment the core of the grains is heated to a temperature of at least 60° C.;

b) wet milling of the oat grains and barley grains resulting from step a) in the presence of an enzyme composition derived from malt, wherein the enzyme composition is heat treated at a temperature in the range of 75 to 80° C. before being provided to the wet milling of step b); and isolating, from the wet milled grains, a beta-glucan enriched fraction by removing, from the wet milled grains, an insoluble fibre enriched fraction.

15. A liquid food product, comprising oat or barley fibre and oat or barley beta-glucan, said food product being obtainable by processing of oat or barley grains according to the process of claim 1.

16. A solid food product, comprising oat or barley fibre, said food product being obtainable by processing of oat or barley grains according to the process of claim 1.

* * * * *